(12) United States Patent
Cornell

(10) Patent No.: US 8,858,515 B2
(45) Date of Patent: Oct. 14, 2014

(54) ANTIMICROBIAL SANITIZER SYSTEM

(71) Applicant: S. Douglas Cornell, Tucson, AZ (US)

(72) Inventor: S. Douglas Cornell, Tucson, AZ (US)

( * ) Notice: Subject to any disclaimer, the term of this patent is extended or adjusted under 35 U.S.C. 154(b) by 0 days.

(21) Appl. No.: 13/707,142

(22) Filed: Dec. 6, 2012

(65) Prior Publication Data

US 2014/0163481 A1    Jun. 12, 2014

(51) Int. Cl.
*A61M 35/00*        (2006.01)

(52) U.S. Cl.
USPC ........................................................ 604/289

(58) Field of Classification Search
CPC .................. A61B 17/24; A61M 35/00; A61M 2025/0226; A61M 2210/0618; A61K 9/0043
USPC .................................................. 604/48, 289
See application file for complete search history.

(56) References Cited

U.S. PATENT DOCUMENTS

| 7,115,275 B2 * | 10/2006 | Clarot et al. ................... 424/434 |
| 2004/0077973 A1 | 4/2004 | Groenke et al. |
| 2004/0176827 A1 * | 9/2004 | Jacobson et al. ............... 607/113 |
| 2005/0182152 A1 * | 8/2005 | Nonninger et al. ........... 523/122 |
| 2007/0143942 A1 * | 6/2007 | Fox et al. ...................... 15/143.1 |
| 2007/0282241 A1 * | 12/2007 | Squires ............................. 604/2 |
| 2008/0060148 A1 | 3/2008 | Pinyayev et al. |
| 2009/0311305 A1 | 12/2009 | Abbott et al. |
| 2010/0034573 A1 | 2/2010 | Moyers |
| 2010/0042137 A1 | 2/2010 | Oronsky et al. |
| 2011/0166508 A1 | 7/2011 | Lyytikainen et al. |
| 2012/0143081 A1 | 6/2012 | Lyu |

OTHER PUBLICATIONS

Biohealth Partnership Publication (2007): Edition 1, March; Lowering Infection Rates in Hospitals and HealthcareFacilities—The Role of Copper Alloys in Battling Infectious Organisms.

* cited by examiner

*Primary Examiner* — Aarti B Berdichevsky

(57) ABSTRACT

An antimicrobial sanitizer system for application of an antimicrobial material on skin or mucous membranes featuring a base handle (110) and a stem extending upwardly from the stem end of the base handle. The stem optionally is extendable from and retractable into an inner cavity in the base handle. The distal end of the stem is rounded and is adapted for insertion into the nasal cavity. At least a portion of the outer surface of the distal end of the stem features an antimicrobial material such as but not limited to copper.

9 Claims, 8 Drawing Sheets

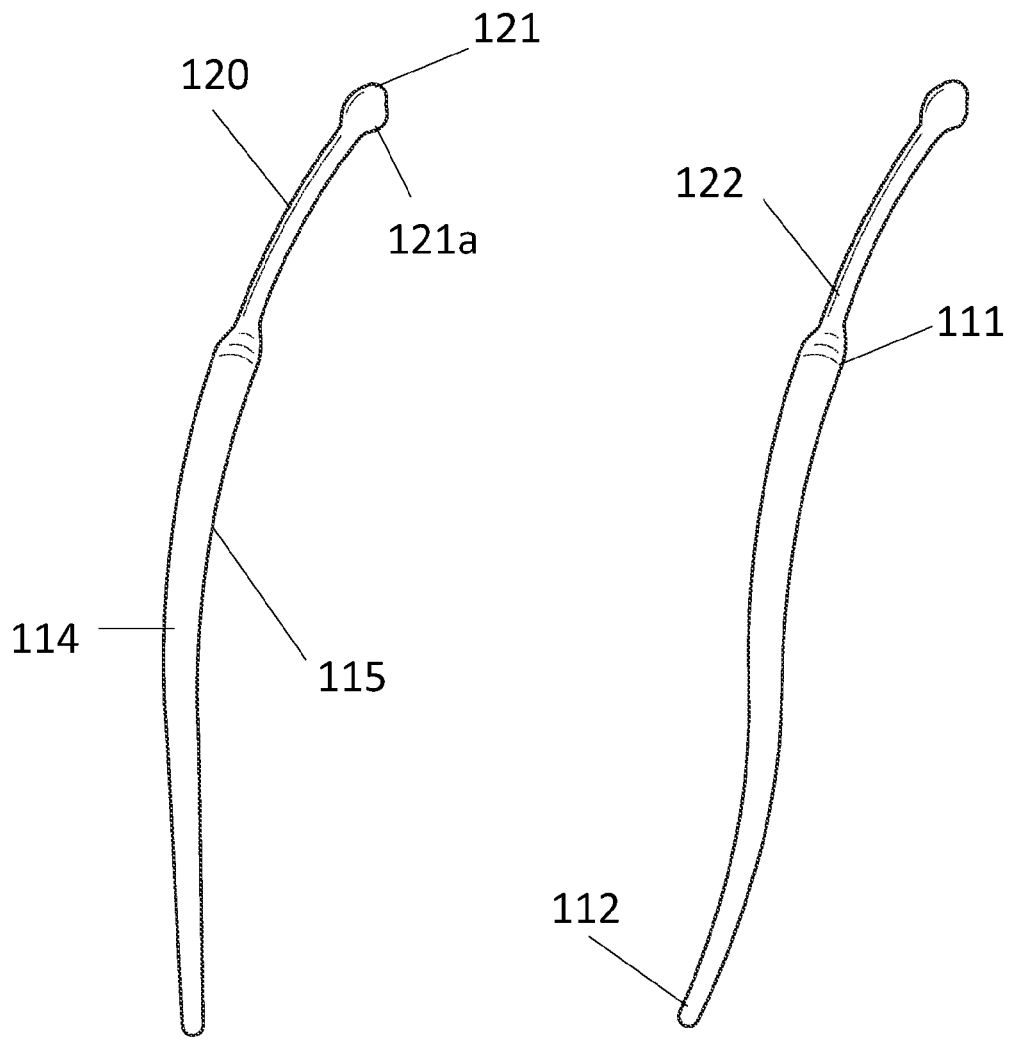
FIG. 3A    FIG. 3B
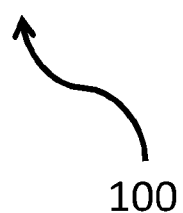

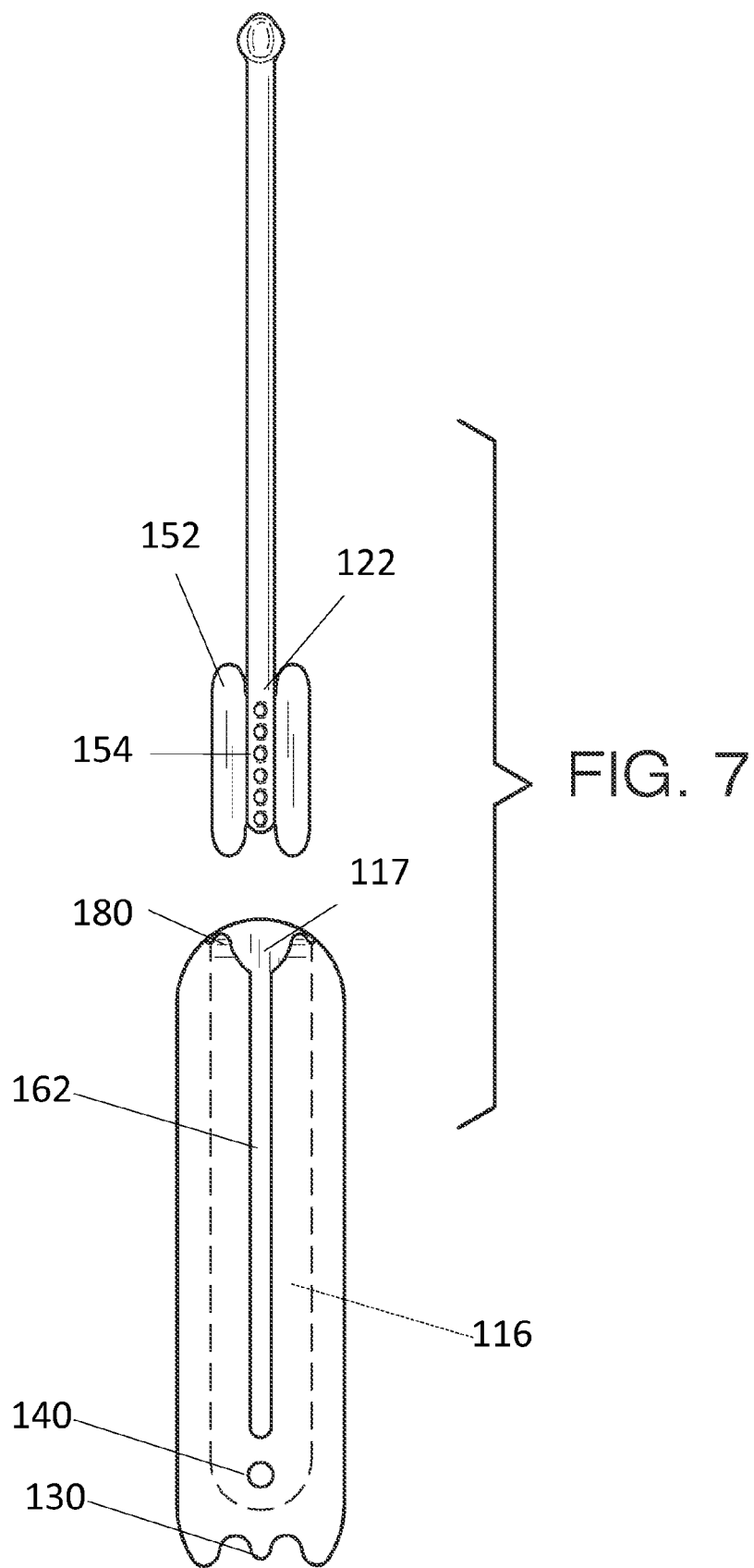

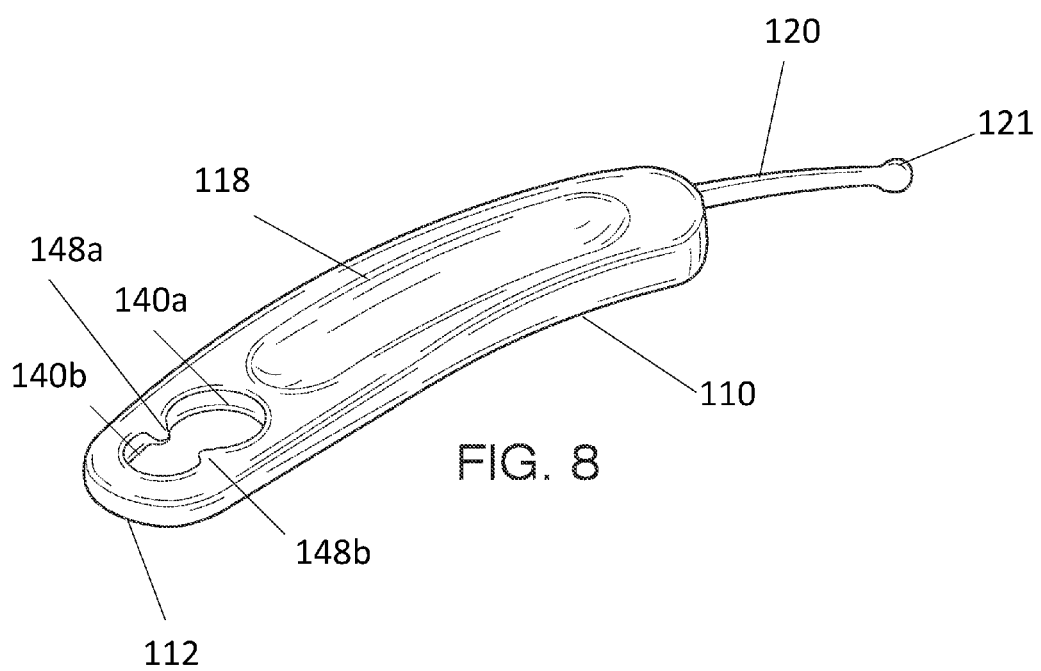

ANTIMICROBIAL SANITIZER SYSTEM

BACKGROUND OF THE INVENTION

The present invention features a novel antimicrobial sanitizer system (e.g., antimicrobial applicator system) for the application of an antimicrobial material to a user's skin and/or to a user's mucous membranes (e.g., in the nose) and/or for attacking pathogens present on skin and/or mucous membranes. Without wishing to limit the present invention to any theory or mechanism, it is believed that during contact with skin or mucous membranes, the system can attack pathogens already present; if the system is rubbed against the skin or mucous membranes, the system deposits a residue of antimicrobial material after contact (for the purpose of killing pathogens). The residue may continue to attack pathogens that are present and may also attack pathogens that arrive subsequently while the residue remains.

Without wishing to limit the present invention to any theory or mechanism, it is believed that the system of the present invention can help reduce the acquisition, development, and/or transmission of infections.

SUMMARY

The present invention features antimicrobial sanitizer systems (e.g., antimicrobial applicator systems) for application of an antimicrobial material on skin or mucous membranes.

In some embodiments, the system comprises a base handle having a stem end, a bottom end opposite the stem end, and a front surface (and a bottom surface, side surfaces); and a stem extending upwardly from the stem end of the base handle. In some embodiments, the stem has a distal end and a proximal end joined or coupled to the base handle. In some embodiments, the distal end is rounded and is adapted for insertion into a nasal cavity. In some embodiments, at least a portion of the outer surface of the distal end of the stem comprises an antimicrobial material.

In some embodiments, the system comprises a base handle having a stem end, a bottom end opposite the stem end, a front surface, and an inner cavity, the inner cavity is accessible via an aperture disposed in the stem end, a slit extends through the front surface of the base handle from the aperture towards the bottom end, the slit has a width smaller than that of the inner cavity; and a stem coupled to the base handle, the stem has a distal end and a proximal end, the distal end is rounded and adapted for insertion into a nasal cavity, the stem is extendable from the stem end of the base handle and retractable into the inner cavity of the base handle, the proximal end of the stem is slidably engaged in the aperture and inner cavity of the base handle. In some embodiments, at least a portion of the outer surface of the distal end of the stem comprises an antimicrobial material.

In some embodiments, at least a portion of an outer surface of the base handle comprises an antimicrobial material. In some embodiments, base handle and/or the stem is constructed as a copper coil. In some embodiments, the base handle and/or the stem is constructed as a solid piece, the solid piece being a solid piece of copper or a solid piece of material coated with copper.

In some embodiments, the stem end of the base handle has a width that is larger than that of the stem. In some embodiments, the stem and the base handle are both arc shaped, the stem has a radius of curvature that is different from that of the base handle.

In some embodiments, the antimicrobial material comprises copper.

In some embodiments, the system further comprises a concave indentation disposed in the front surface of the base handle extending from at or near the stem end to at or near the bottom end of the base handle. In some embodiments, an inward curvature is disposed in the bottom end of the base handle, and a flange extends downwardly from the inward curvature, the flange is adapted to be inserted under a user's fingernail.

In some embodiments, the system further comprises a hole disposed in the base handle adapted to accept a string or a lanyard.

In some embodiments, the system further comprises a tongue extending outwardly from sides of the proximal end of the stem, wherein the tongue engages the inner cavity of the base handle. In some embodiments, the system further comprises friction nubs disposed on a front surface of the stem at or near the proximal end, wherein the friction nubs protrude through the slit of the base handle, wherein the friction nubs provide a surface for gripping the stem to allow retraction and extension of the stem. In some embodiments, the system further comprises retention tabs disposed on the front surface of the base handle surrounding the aperture, wherein the retention tabs prevent the stem from disengaging the base handle.

The present invention also features an antimicrobial applicator system comprising: a base handle having a stem end, a bottom end opposite the stem end, and a front surface; a stem extending upwardly from the stem end of the base handle, the stem has a distal end and a proximal end joined or coupled to the base handle, the distal end is rounded and is adapted for insertion into a nasal cavity; a concave indentation disposed in at least the front surface of the base handle extending from at or near the stem end to at or near the bottom end of the base handle; and a hole disposed in the base handle adapted to accept a string or a lanyard, the hole comprises a first cavity and a second cavity opposite the first cavity; wherein at least a portion of an outer surface of the distal end of the stem comprises an antimicrobial material.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 3A is a side view of an embodiment of the system of the present invention. An arc shape of the stem and the base handle is shown.

FIG. 3B is a side view of an embodiment of the system of the present invention. An arc shape of the stem and the base handle is shown.

FIG. 7 is a front view of an embodiment of the system of the present invention. The stem is optionally retractable.

FIG. 8 is a perspective view of an embodiment of the system of the present invention.

DESCRIPTION OF PREFERRED EMBODIMENTS

Figure 1:
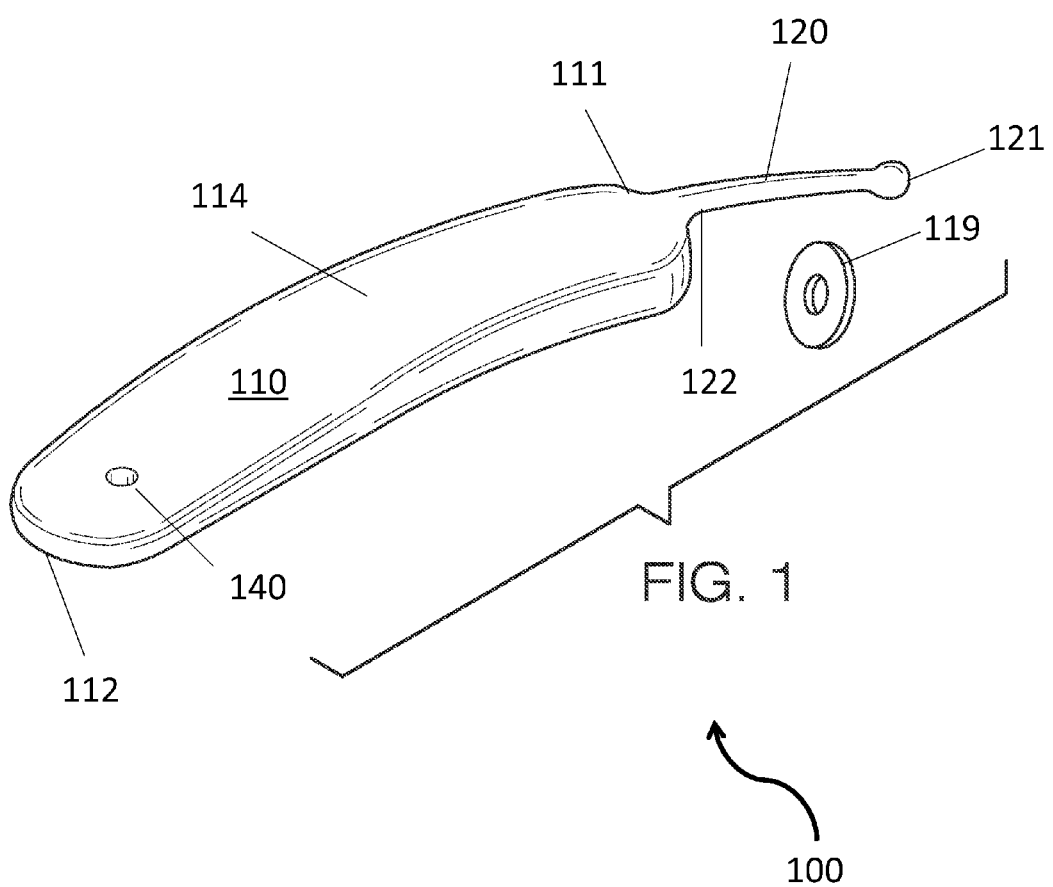
FIG. 1 is a perspective view of an embodiment of the system of the present invention.

Referring now to FIG. 1-8, the present invention features an antimicrobial sanitizer system (e.g., an antimicrobial applicator system (100)) for application of an antimicrobial material on a user's skin and/or mucous membranes. The system (100) comprises a base handle (110) and a stem (120) extending from the base handle (110). The stem (120) is optionally retractable into and extendable from the base handle (110). The base handle (110) may be used to apply antimicrobial material to a user's hands and fingers, face, or other body part. The stem (120) may be used to apply antimicrobial material to mucous membranes (e.g., where microorganisms lodge) such as the nasal cavity. In some embodiments, the antimicrobial material comprises copper. The antimicrobial material is not limited to copper.

The base handle (110) has a stem end (111) (e.g., a "shoulder"), a bottom end (112) opposite the stem end (111), a front surface (114), and a back surface (115). The directional terms "bottom," "front," and "back" (e.g.; referring to the surfaces and ends of the base handle) are for reference only and are used for descriptive purposes only. The stem (120) extends from the stem end (111) of the base handle (110).

The base handle (110) may be constructed in a variety of shapes not limited to the shapes shown in the figures. For example, in some embodiments, the base handle (110) has rounded edges, for example for providing a comfortable rounded and smooth surface that can be rubbed on a user's face, hands (e.g., palms, fingers, etc.) or other body part. In some embodiments, the base handle (110) has an elongated shape, slightly rectangular with rounded edges. In some embodiments, the base handle (110) is arc-shaped (when viewed from the side, see FIG. 3A, FIG. 3B). In some embodiments, the base handle (110) is arc-shaped with two arcs in opposite directions (e.g., joined by an inflection point) as shown in FIG. 3B. In some embodiments, the stem end (111) of the base handle (110) has a width wider than that of the stem (120). In some embodiments, all or a portion of the base handle (110) has a width wider than that of the stem (120).

Figure 2:
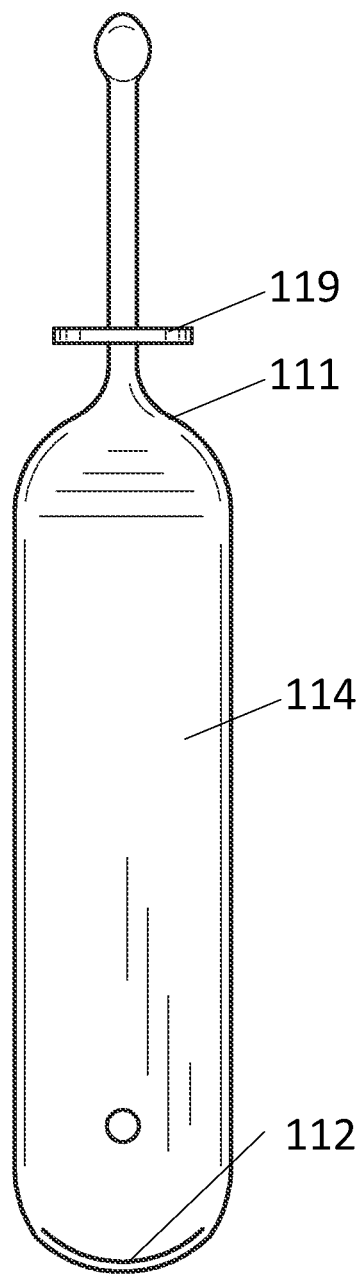
FIG. 2 is a front view of an embodiment of the system of the present invention.

In some embodiments, the stem end (111) (e.g., shoulder) of the base handle (110) helps to restrict how far into the nasal cavity the stem (120) extends. This limitation can help prevent damage to the user's nasal cavity by extending the stem (120) too far into the nasal cavity. As shown in FIG. 2, in some embodiments, a stopper (119) is disposed on the stem (120), e.g., near the stem end (111) of the base handle (110) functioning to restrict how far into the nasal cavity the stem (120) extends. For example, in lieu of using the stem end (111) of the base handle (110) to restrict extension of the stem (120) into the nasal cavity, the stopper (119) may serve that purpose. In some embodiments, the stopper (119) is removable from the stem (120) (FIG. 1 shows the stopper (119) removed from the stem (120)).

The system (100) further comprises a stem (120) extending upwardly from the stem end (111) of the base handle (110). The stem (120) has a distal end (121) and a proximal end (122), the proximal end (122) being the end that is joined to or attached to (or coupled to) the base handle (110). The distal end (121) is rounded and is adapted for insertion into the nasal cavity, e.g., the distal end (121) is a bulb or knob. In some embodiments, the distal end (121) of the stem (120) is oval or spherical, however the distal end (121) of the stem (120) is not limited to an oval or spherical configuration. For example, in some embodiments, the distal end (121) of the stem (120) is spherical with a ridge or protrusion (121*a*) for reaching into a narrower or deeper portion of the nasal cavity. In some embodiments, the protrusion (121*a*) is disposed on the bottom surface of the distal end (121) of the stem (120), e.g., the end aligned with the bottom surface (115) of the base handle (110) (however, the position and orientation of the protrusion (121*a*) is not limited to the aforementioned configuration or the configurations shown in the figures). In some embodiments, the distal end (121) of the stem (120) has a width larger than that of the proximal end (122) of the stem (120). In some embodiments, the distal end (121) of the stem (120) has a width larger than that of the middle portion of the stem (120), e.g., the portion in between the proximal end (122) and the distal end (121).

At least a portion of the outer surface of the distal end (121) of the stem (120) comprises an antimicrobial material. For example, in some embodiments, the stem (120) is constructed entirely from the antimicrobial material (e.g., copper). In some embodiments, the stem (120) is constructed from a material that is coated with the antimicrobial material (e.g., copper). In some embodiments, the entire outer surface of the stem (120) features exposed antimicrobial material (e.g., copper). In some embodiments, only a portion of the outer surface of the stem (120) features exposed antimicrobial material (e.g., copper).

In some embodiments, at least a portion of an outer surface of the base handle (110) comprises an antimicrobial material. For example, in some embodiments, the base handle (110) is constructed entirely from the antimicrobial material (e.g., copper). In some embodiments, the base handle (110) is constructed from a material that is coated with the antimicrobial material (e.g., copper). In some embodiments, the entire outer surface of the base handle (110) features exposed antimicrobial material (e.g., copper). In some embodiments, only a portion of the outer surface of the base handle (110) features exposed antimicrobial material (e.g., copper).

The base handle (110) and stem (120) may be constructed in a variety of configurations. For example, in some embodiments, the base handle (110) and/or the stem (120) is constructed as a solid piece, for example a solid piece of copper, a solid piece of material (e.g., plastic) coated with copper. In some embodiments, the base handle (110) and/or the stem (120) is constructed as a coil, e.g., a copper coil.

In some embodiments, the base handle (110) is curved or arc-shaped (see FIG. 3A, FIG. 3B). In some embodiments, the stem (120) is curved or arc-shaped (see FIG. 3A, FIG. 3B). The curvature of the stem (120) may help the distal end (121) of the stem (120) to reach a particular portion of the nasal cavity, for example the inferior meatus.

In some embodiments, the base handle (110) is arc shaped and has an arc length of between about 3 to 8 inches, for example about 3 inches, about 3.5 inches, etc. In some embodiments, the base handle (110) is arc shaped and has an arc length of between about 4 to 10 inches. In sonic embodiments, the base handle (110) is arc shaped and has an arc length of between about 4 to 6 inches. The arc length of the base handle (110) is not limited to the aforementioned examples. For example, in some embodiments such as the embodiments with the retractable stem (120) described below, the base handle (110) has an arc length of about 3.5 inches.

In some embodiments, the base handle (110) is arc shaped and has radius of curvature of between about 5 to 14 inches, e.g., 7 inches, 5.5 inches, etc. In some embodiments, the base handle (110) is arc shaped and has radius of curvature of between about 8 to 20 inches. In some embodiments, the base handle (110) is arc shaped and has radius of curvature of between about 6 to 30 inches. In some embodiments, the base handle (110) is arc shaped and has radius of curvature of between about 10 to 30 inches. The radius of curvature of the base handle (110) is not limited la the aforementioned examples.

In some embodiments, the stem (120) is arc shaped and has an arc length of between about 0.5 to 5 inches, for example about 2 inches, about 3 inches. In some embodiments, the stem (120) is arc shaped and has an arc length of between about 1 to 3 inches. In some embodiments, the stem (120) is arc shaped and has an arc length of between about 1.5 to 3 inches. The arc length of the stem (120) is not limited to the aforementioned examples. For example, in some embodiments such as the embodiments with the retractable stem (120) described below, the stem (120) has an arc length of about 3 inches overall but only about 2 inches of the stem (120) extend beyond the base handle (110).

In some embodiments, the stem (120) is arc shaped and has radius of curvature of between about 4 to 12 inches, e.g., 5 inches. In some embodiments, the stem (120) is arc shaped and has radius of curvature of between about 8 to 20 inches. In some embodiments, the stem (120) is arc shaped and has radius of curvature of between about 6 to 30 inches. In some embodiments, the stem (120) is arc shaped and has radius of curvature of between about 10 to 30 inches. The radius of curvature of the stem (120) is not limited to the aforementioned examples.

In some embodiments, the base handle (110) may not have a constant radius of curvature. For example, in some embodiments, one portion of the base handle (110) may have a first radius of curvature and a second portion of the base handle (110) may have a second radius of curvature. In some embodiments, the base handle (110) has a S-shape wherein the direction of the curvature changes (e.g., via an inflection point) (see FIG. 3B). In some embodiments, the stem (120) is part of the S-shape, e.g., the S-shape includes the stem (120).

In some embodiments, the stem (120) may not have a constant radius of curvature. For example, in some embodiments, one portion of the stem (120) may have a first radius of curvature and a second portion of the stem (120) may have a second radius of curvature.

In some embodiments, the stem (120) and the base handle (110) are both arc shaped and the stem (120) has a radius of curvature that is different from that of the base handle (110).

Figure 4:
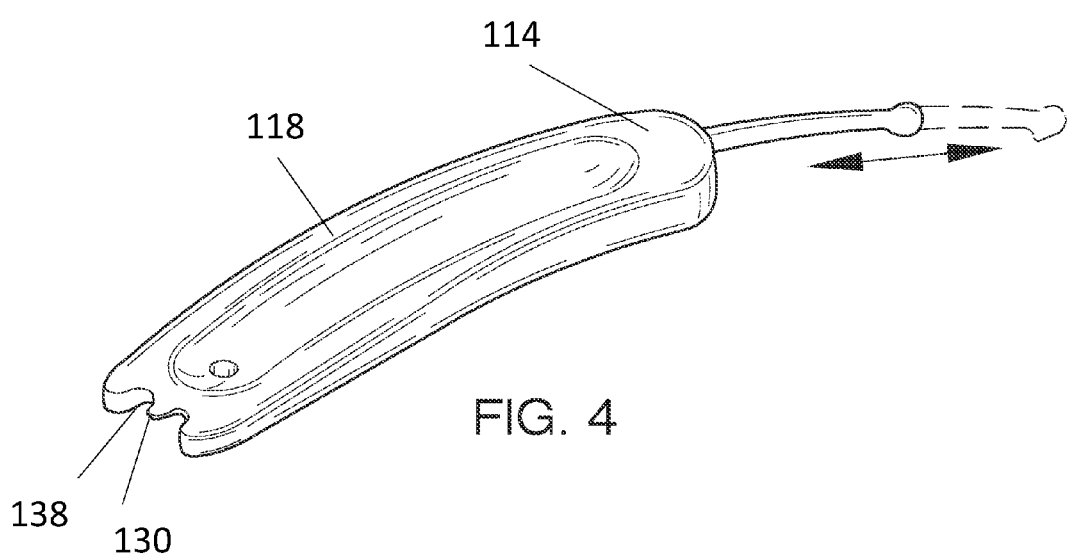
FIG. 4 is a perspective view of an embodiment of the system of the present invention. The stem is optionally retractable.

As shown in FIG. 4, in some embodiments, the front surface (114) of the base handle (110) is curved inwardly, e.g., the front surface (114) comprises a concave indentation (118). The concave indentation (118) may extend from at or near the stem end (111) to at or near the bottom end (112) of the base handle (110). The concave indentation (118) may function to provide additional surface area to the front surface (114) of the base handle (110), e.g., to provide more area on which a user can rub his/her fingers, palms, or other body part. A user may choose to rub his/her hands and/or fingers along the front surface (114), e.g., the concave indentation (118) and/or the back surface (115) of the base handle (110).

In some embodiments, the system (100) further comprises a concave indentation disposed in the back surface (115) of the base handle (110), e.g., concave indentations are disposed in both the front surface (114) and back surface (115) of the base handle (110). The concave indentation (118) in the back surface (115) may extend from at or near the stem end (111) to at or near the bottom end (112) of the base handle (110).

The concave indentation (118) in the back surface (115) of the base handle (110) may function to provide additional surface area to the back surface (115) of the base handle (110), e.g., to provide more area on which a user can rub his/her fingers, palms, or other body part. In some embodiments, a user may use one indentation for his/her thumb and the opposite indentation for his/her fingers.

As shown in FIG. 4, in some embodiments, the system (100) further comprises a flange (130) extending from a surface of the base handle (110). For example, in some embodiments, the flange (130) extends downwardly from the bottom end (112) of the base handle (110). In some embodiments, the flange (130) extends outwardly from a side of the base handle (110). The flange (130) is not limited to placement on the bottom end (112) or a side of the base handle (110) and may be situated on any appropriate surface of the base handle (110). The flange (130) is adapted to be inserted under a user's fingernail or other appropriate location. In some embodiments, an inward curvature (138) is disposed at the location of the flange (130) and the flange (130) extends from the inward curvature. For example, in some embodiments, the inward curvature (138) is disposed in the bottom end (112) of the base handle (110) and the flange (130) extends downwardly from the inward curvature (138). In some embodiments, the flange (130) does not extend beyond the bottom end (112) of the base handle (110) or the adjacent surface of the base handle (110) depending on the location of the flange (130).

In some embodiments, the system (100) further comprises a hole (140) disposed in the base handle (110) adapted to accept a string or a lanyard. The hole (140) may be constructed in a variety of shapes and sizes. For example, in some embodiments, the hole (140) is circular in shape (as viewed from the front surface (114) as shown in FIG. 2. In some embodiments, the hole (140) is an alternative shape as shown in FIG. 8. For example, the hole (140) may have a generally hourglass shape (as shown in FIG. 8). For example, the hole (140) may comprise two cavities, e.g., two opposing cavities, e.g., a first cavity (140a) and a second cavity (140b). The cavities (140) may be separated by a first cavity protrusion (148a), which extends a distance into the hole (140). In some embodiments, the cavities (140) are also separated by a second cavity protrusion (148b), which extends a distance into the hole (140). In some embodiments, the cavity protrusions (148) are opposite each other (as shown in FIG. 8). In some embodiments, the cavity protrusions (148) are not opposite each other. The hole (140) may be constructed in any appropriate shape and is not limited to the examples shown in the figures.

Figure 5:
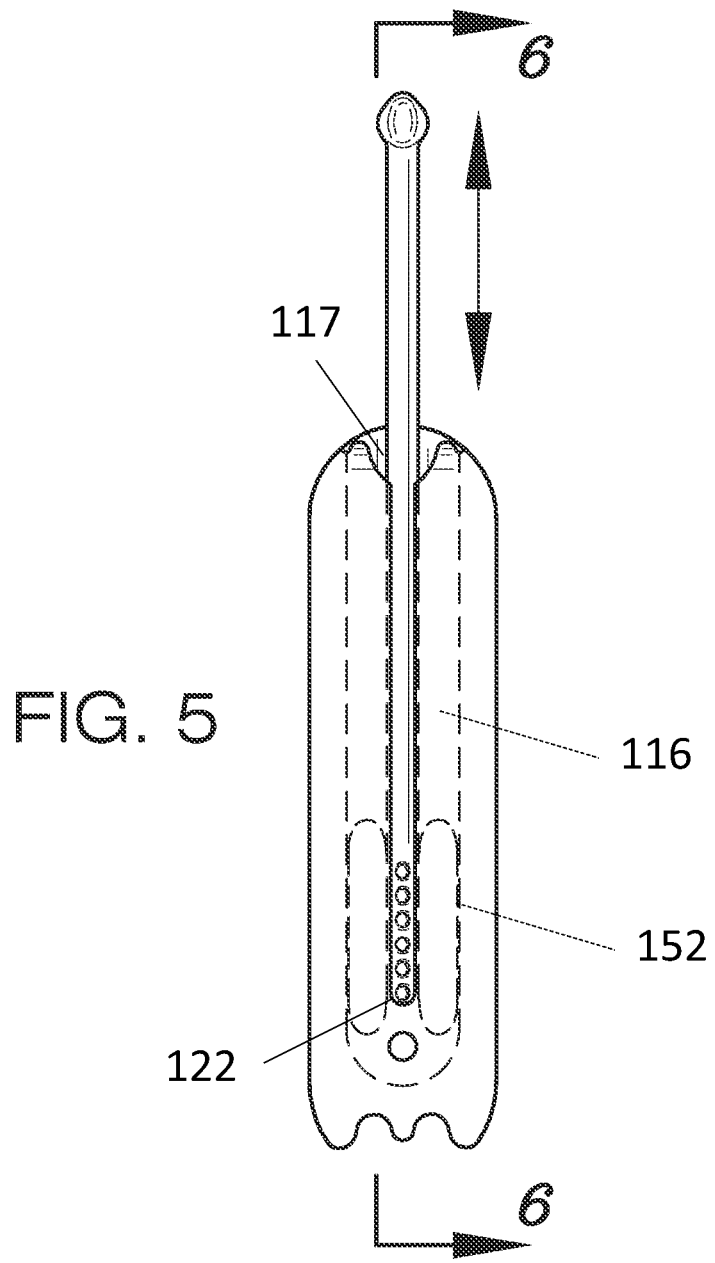
FIG. 5 is a front view of an embodiment of the system of the present invention. The stem is optionally retractable.
Figure 6:
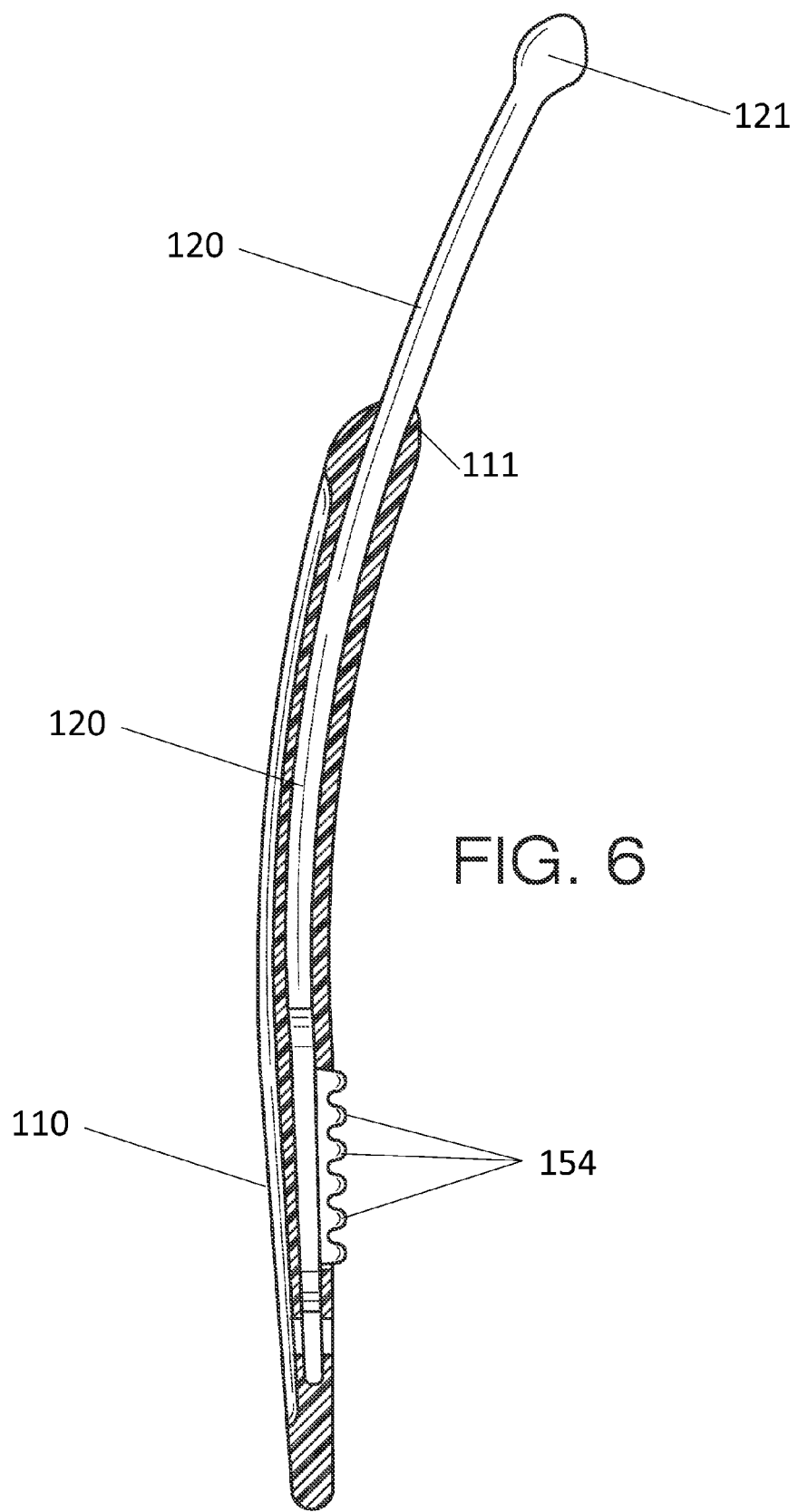
FIG. 6 is a side and partial cross sectional view of an embodiment of the system of the present invention. The stem is optionally retractable.

The antimicrobial applicator system may feature a retractable and extendable stem (120) coupled to the base handle (110). For example, as shown in FIG. 5, FIG. 6, and FIG. 7, in some embodiments, the base handle (110) has an inner cavity (116), which is accessible via an opening or aperture (117) disposed in the stem end (111) of the base handle (110). The inner cavity (116) is adapted to accept the stem (120), e.g., the proximal end (122) of the stem (120). For example, the proximal end (122) of the stem (120) may be slidably engaged in the aperture (117) and inner cavity (116) of the base handle (110). In some embodiments, the stem (120) is extendable from the stem end (111) of the base handle (110) and retractable into the inner cavity of the base handle (110).

As shown in FIG. 7, in some embodiments, a slit (162) is disposed in the front surface (114) of the base handle (110) and extends from the aperture (117) towards the bottom end (112) of the base handle (110). The slit (162) has a width smaller than that of the inner cavity (116) of the base handle (110). In some embodiments, the slit (162) has a width smaller than that of the stem (120). In some embodiments, one or more friction nubs (154) are disposed on the front surface of the stem (120) (e.g., at or near the proximal end (122)) wherein the friction nub(s) (154) protrude through the slit (162). The friction nubs (154) may provide a surface for helping a user grip the stem (120) to allow retraction and extension of the stem (120). For example, a user can slide the friction nub (154) upwardly and downwardly within the slit (162) to respectively extend the stem (120) from and retract the stem (120) into the base handle (110). FIG. 6 shows the friction nubs (154) protruding through the slit (162).

In some embodiments, a tongue (152) extends outwardly from one or both sides of the proximal end (122) of the stem (120). The tongue (152) engages the inner cavity (116) of the base handle (110). The tongue (152) helps retain the stem (120) in the inner cavity (116) of the base handle (110) in the presence of the slit (162). For example, because the slit (162) is narrower than the width of the stem (120) with the tongue (152), the stem (120) with the tongue (152) is retained in the inner cavity (116) of the base handle (110).

As shown in FIG. 5 and FIG. 7, in some embodiments, the base handle (110) comprises retention tabs (180) for helping prevent the stem (120) (e.g., with tongue) from sliding all of the way out of the inner cavity (116) and separating from (disengaging) the base handle (110). In some embodiments, retention tabs (180) are disposed on the front surface (114) of the base handle (110) surrounding the aperture (117). For example, a first retention tab (180) may be disposed at the intersection of the front surface (114) of the base handle (110) and the aperture (117) on one side of the slit (162). A second retention tab (180) may be disposed at the intersection of the front surface (114) of the base handle (110) and the aperture (117) on a second side of the slit (162). The retention tabs (180) may fold toward the back surface (115) of the base handle, e.g., over the inner cavity, over the aperture (117), etc.

In some embodiments, the stem (120) is flexible to help the retraction into the base handle (110) and extension from the base handle (110).

As used herein, the term "about" refers to plus or minus 10% of the referenced number. For example, an embodiment wherein the stem has an arc length of about 2 inches includes a stem with an arc length of between 1.8 and 2.2 inches.

EXAMPLES

Example 1

Use of Sanitizer System in Hospital Setting

A Nurse or Doctor carries the presently claimed Sanitizer System in her coat jacket pocket or on a lanyard around her neck. The System is made of a copper alloy recognized by the Environmental Protection Administration (EPA) as having antimicrobial properties in certain applications.

On the way to a ward or to a patient's room, the Nurse or Doctor rubs her fingers and thumb on the Sanitizer System, which is believed to help kill any pathogens that may be present, thus reducing her chance of transmitting a live pathogen to a patient. The rubbing also lays down a residue of copper, which is believed to help kill any pathogens she may pick up from a patient or from items she touches in the room. She may also swab the tip of the wand in the vestibule of her nostrils and rub the edges of the base portion of the system on her nose and face to further lay down a residue of copper alloy. This may further reduce the chance of her acquiring an infectious illness in case she touches her face with a fingertip that might at that moment be host to a live pathogen.

The curvature of the front and back of the base, or handle, of the System increases the surface area of contact between the antimicrobial material of the surface of the System and the skin of the user. The design is intended to maximize such contact when the System is held in the hand. In addition, the curvatures of the edges of the base, or handle, are designed to make it comfortable and easy to rub against the face and nose, including the skin over the cheekbones, the lips, and the underside of the nostrils, in a manner that can effectively reach all the facial surfaces, concave, convex, and otherwise. The flanges in some embodiments of the System are designed to allow rubbing of the antimicrobial material under the fingernails and thumbnails with maximum convenience. The entire shape of the System is designed to allow one-handed use, while walking, by a busy health care worker who may be carrying things in the other hand and who is likely to be in a hurry.

Most infectious illnesses are transmitted by touch. Since people naturally touch their face unconsciously many times a day, it is easy for a pathogen to travel from fingertip to face and thence to the nose and into the body. A residue of antimicrobial material on fingers, face and nose may inhibit this route of transmission. In addition, it may reduce the chance she may transmit the pathogen to others. In addition, application of the System in the nostril may inhibit the acquisition of airborne pathogens.

Immediately after contact with the patient, if the Nurse or Doctor does not have an opportunity to wash her hands right away, she rubs the Sanitizer System again to increase the potential kill rate of any pathogens she may have picked up. The residue is absorbed by skin and mucous membranes over a period of about half an hour, so it is only a temporary shield and should be renewed frequently by further rubbing.

Use of the System in a health care setting is in addition to, rather than a substitute for, EPA-recommended use of Antimicrobial Copper (trademark of the Copper Development Association) in "touch-surfaces" in hospitals, such as bedrails, doorknobs, call buttons, faucets, light switches, etc. Tests by the EPA and others show Antimicrobial Copper inhibits or kills, on contact in minutes, a wide variety of dangerous bacteria and viruses, including MRSA, VRE, C. Diff, *E. Coli*, Influenza A, H1N1, Rhinovirus, Adenovirus, and others.

Example 2

Use of Sanitizer System while Traveling on Public Commuter Systems

A passenger carries the Sanitizer System on his person. Just prior to entering a plane, train, or bus, he uses it in a similar manner to the Nurse or Doctor in Example 1, at least on the fingers and thumbs. He uses it again just before and just after touching various surfaces known to harbor potential pathogens, such as airplane tray tables and lavatory fixtures. Assiduous use may reduce the chance not only of acquiring pathogens but also of spreading them.

Example 3

Use of Sanitizer System while Shopping

In the process of shopping, a person comes in contact with a wide array of microbes on everything from items for sale to credit cards. Paper money is especially known to carry many bacteria and viruses. Even if a shopper doesn't use paper money, she touches objects that have been handled by store clerks who, as part of their job, must handle paper money from many other customers, some of whom may be carrying infectious illnesses.

The shopper may use the system on fingers and thumbs in a manner similar to the Nurse or Doctor in Example 1 before and after shopping and before and after each instance of handling money. Shoppers may be disinclined to use the System of their faces or in their nostrils in public, but it may be less important to do so in a store than in a health care setting, especially if the shopper makes an effort to avoid touching her face until after she returns home and washes her hands thoroughly. Use of the System is never a substitute for regular and thorough hand-washing.

Example 4

Use of Sanitizer System in Day Care and School Settings

A day care worker or a school teacher may use the System in a manner similar to the Nurse or Doctor in Example 1 at frequent intervals through the workday. In addition to potentially protecting themselves and the children in their care, the worker or teacher may also reduce the risk of bringing home infectious pathogens and spreading illness to their own families.

Example 5

Use of Sanitizer System in Elder Care Facilities

It is known that outbreaks of flu or other infectious illness in elder care facilities may start with one visitor or staff member and spread to residents, then to other staff members, and to other visitors and their families. Staff members and visitors may use the System in a manner similar to the Nurse or Doctor in Example 1 before and after contact with residents, to potentially help protect themselves and everyone else involved.

Example 6

Use of Sanitizer System to Fight Off the Common Cold or Flu

A cold or flu often starts with a tickle in the nose, which signals the accumulation of Rhinovirus or Adenovirus in the inner cavity of the nostril. Sometimes cold or flu may start with a scratchy throat, which signals the same thing and results from virus-containing mucous dripping from the nostril backwards into the throat.

Upon any early sign of cold or flu, a user may gently rub the tip of the wand of the Sanitizer System in the inner cavity of the nostril, especially in the bottom of the cavity, known as the inferior meatus, where the cold or flu virus may first accumulate and replicate. The copper begins killing the cold or flu virus immediately. The copper residue left after 30 seconds or a minute of rubbing is believed to continue killing the virus after the wand is removed.

The effect is believed to be similar to that of zinc-containing gel, once sold under the trade name Zicam. Zinc has antimicrobial properties akin to those of copper. Both copper and zinc kill cold and flu viruses on contact in minutes. If used early enough, they are believed to reduce the virus population in the nostril and inhibit its replication. Suppression of the virus numbers can allow the immune system to gain the upper hand quickly and fully defeat the cold or flu in the first day or two, before any major symptoms develop.

Despite its effectiveness, Zicam was removed from the market by the FDA after it was determined that Zicam could damage the sense of smell of the user, sometimes permanently. It is believed that the damage resulted from inhalation of quantities of the zinc gel, which drew significant quantities of zinc deep into the nostril and brought it into contact with the olfactory nerves, which control the sense of smell. The Sanitizer System limits the length of the wand so that it cannot reach the olfactory nerves and does not deposit significant quantities of material, thus avoiding the threat to the sense of smell. The System is not recommended for use by persons under the age of 12, however, due in part to the risk of reaching the tip of the wand all the way to the olfactory nerves in a child-sized nose, just in case the slight copper residue might damage the nerves.

In some embodiments, the System may use zinc instead of copper. Copper, however, may be more effective than zinc due in part to greater electrical conductivity, which is thought to be a factor in its anti-pathogen effect. Copper is also believed to have a higher threshold of toxicity than zinc. Copper is contained in many foods and is part of a healthy diet.

The earlier the System is used in the development of the cold or flu, the greater the chance of stopping the illness before it takes hold. The user gently rubs the tip of the wand for up to a minute on the mucous membranes that line the inner cavity of the nostril. The user may do so again in half an hour or so, and perhaps a third or fourth time at half hour intervals if the tickle in the nose or the scratchy throat returns or has not been completely eliminated.

In all examples, it is important that the user keep the Sanitizer System clean and free of dirt, oil, film, or other foreign matter. Copper is known to kill pathogens by direct physical contact of the copper surface with the individual bacterium or virus. Thus any foreign matter on the surface of the System may reduce its effectiveness.

Though the System is designed based in part on results of studies of "Antimicrobial Copper", the inventor at present does not apply the term "Antimicrobial Copper" to the System. The term is a trade name of the Copper Development Association which, in conjunction with the EPA, sets requirements for its use.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application; and are exemplary, and are not intended in any way to limit the scope of the claims to the particular features having the corresponding reference numbers in the drawings.

What is claimed is:

1. An antimicrobial applicator system (100) for application of an antimicrobial material on skin or mucous membranes, said system (100) comprising:
   (a) a base handle (110) having a stem end (111), a bottom end (112) opposite the stem end (111), a front surface (114), and a back surface (115), wherein the base handle (110) is arc-shaped from the stem end (111) to the bottom end (112), wherein a concave indention is disposed on the front surface (114) or the back surface (115) from a point proximal to the stem end (111) to a point proximal to the bottom end (112); and (b) a stem (120) extending upwardly from the stem end (111) of the base handle (110), the stem (120) has a distal end (121) and a proximal end (122) joined or coupled to the base handle (110), the distal end (121) is bulbous and is adapted for insertion into a nasal cavity, wherein a ridge is longitudinally disposed a bottom surface of the bulbous distal end (121), wherein the stem (120) is arc-shaped from the distal end (121) to the proximal end (122);

wherein at least a portion of the stem (120) or the base handle (110) is constructed from an antimicrobial material.

2. The system (100) of claim 1, wherein at least a portion of an outer surface of the base handle (110) comprises an antimicrobial material.

3. The system (100) of claim 1, wherein the base handle (110) is constructed as a copper coil.

4. The system (100) of claim 1, wherein the base handle (110) is constructed as a solid piece, the solid piece being a solid piece of copper or a solid piece of material coated with copper.

5. The system (100) of claim 1, wherein the stem end (111) of the base handle (110) has a width that is larger than that of the stem (120).

6. The system (100) of claim 1, wherein the stem (120) and the base handle (110) are both arc shaped, the stem (120) has a radius of curvature that is different from that of the base handle (110).

7. The system (100) of claim 1, wherein the antimicrobial material comprises copper.

8. The system (100) of claim 1, wherein an inward curvature (138) is disposed in the bottom end (112) of the base handle (110), and a flange (130) extends downwardly from the inward curvature, the flange is adapted to be inserted under a user's fingernail.

9. The system (100) of claim 1 further comprising a hole (140) disposed in the base handle (110) adapted to accept a string or a lanyard.

* * * * *